United States Patent [19]
Sato et al.

[11] Patent Number: 5,958,419
[45] Date of Patent: Sep. 28, 1999

[54] ANTIHISTAMINIC SUBSTANCE OF STEVIA ORIGIN

[75] Inventors: Minoru Sato; Masaaki Takeuchi, both of Miyagi-ken; Naohiko Sato, Tokyo, all of Japan

[73] Assignee: Naohiko SATO, Tokyo, Japan

[21] Appl. No.: 09/038,861

[22] Filed: Mar. 11, 1998

[30] Foreign Application Priority Data

Mar. 31, 1997 [JP] Japan .................................. 9-094397

[51] Int. Cl.$^6$ .................................................. A01N 65/00
[52] U.S. Cl. ........................................................ 424/195.1
[58] Field of Search .......................................... 424/195.1

[56] References Cited

U.S. PATENT DOCUMENTS

| | | | |
|---|---|---|---|
| 3,723,410 | 3/1973 | Persinos .................................. | 536/18.2 |
| 4,082,858 | 4/1978 | Morita et al. ........................... | 536/18.1 |
| 4,361,697 | 11/1982 | Dobberstein et al. .................. | 536/127 |
| 4,599,403 | 7/1986 | Kumar .................................... | 536/18.1 |
| 5,112,610 | 5/1992 | Kienle .................................... | 424/195.1 |
| 5,250,301 | 10/1993 | Dozono .................................. | 424/195.1 |
| 5,262,161 | 11/1993 | Dozono .................................. | 424/195.1 |
| 5,635,611 | 6/1997 | Ishiguro et al. ........................ | 536/51 |

FOREIGN PATENT DOCUMENTS 5-25740  2/1993  European Pat. Off. .

OTHER PUBLICATIONS

Database WPI Section Ch, Week 9805, Derwent Publications Ltd., London, GB; Class B05, AN 98–042992, XP002064307 & CN 1 137 381 A (Beijing Ultramicrobiological Prod Co Ltd) * abstract*.

Database WPI Section Ch, Week 9712, Derwent Publications Ltd., London, GB; Class B04, AN 97–119937, XP002064308 & CN 1 080 864 A (Shenyang College Pharmacy) *abstract*.

Database WPI Section Ch, Week 9718, Derwent Publications Ltd., London, GB; Class B05, AN 97–197202, XP002064309 & JP 09 052 827 A (Taisho Pharm Co Ltd) *abstract*.

Patent Abstracts of Japan vol. 097, No. 004, Apr. 30, 1997 & JP 08 325156 A (Ichimaru Pharcos Co Ltd), Dec. 10, 1996, *abstract*.

*Primary Examiner*—Herbert J. Lilling
*Attorney, Agent, or Firm*—Jordan and Hamburg LLP

[57] ABSTRACT

An antihistaminic substance comprising an extract from a plant tissue of Stevia, which is primarily contained in its stems and leaves, and in a cold water, hot water or lower alcohol extract thereof. Standing of the extract naturally causes fermentation to separate one or more organic acids such as lactic acid and acetic acid, thereby more enhancing the antihistaminic action. The addition of at least one organic acid to the extract immediately after extraction can also enhance the antihistiminic action. When rainbow trout or broilers are fed diets containing histamine, this extract significantly relieves the action of histamine. The extract also represses symptoms such as flare, itch and pain caused by excessive release of activated histamine or a histaminic substance, thus providing an antihistaminic substance of natural origin having no side effects.

7 Claims, 3 Drawing Sheets

ANTIHISTAMINIC SUBSTANCE OF STEVIA ORIGIN

FIELD OF THE INVENTION

The present invention relates to an antihistaminic substance of Stevia origin having the action of repressing various harmful effects to animal organs caused by histamine excessively released from histamine release cells.

BACKGROUND OF THE INVENTION

Recently, pollen has been produced in large amounts by excessive tree planting of Japanese cedars and Japanese cypresses. Moreover, industrialization has increased air pollution or the amount of chemical substances released, so that pollenosis, which is an allergic disease due to combined pollution of the chemical substances and the pollen, has been widely spread. Against such an allergic disease, masks are worn. However, the wearing of masks is only symptomatic therapy, and it is impossible to prevent infection through eyes which can not be covered with masks.

On the other hand, stevioside and rebaudioside, primarily contained in leaves of Stevia, have a strong sweet taste in small amounts, and are used as natural sweeteners low in calories in substitution for sugar. Stevia is therefore known as a raw material for natural sweeteners low in calories.

As oral drugs antagonistic against histamine, drugs containing antihistaminic agents such as diphenhydramine hydrochloride and promethazine are commercially available. However, the antihistaminic agents generally have the side effect that they cause drowsiness, which results in a decisive disadvantage when patients tackle work and study enthusiastically.

It is desirable to have substances of natural origin for relieving symptoms of allergic diseases, which have no side effect such as drowsiness and can be continuously given without anxiety of a side effect.

SUMMARY OF THE INVENTION

An object of the present invention is to solve the above-mentioned problem and to provide an antihistaminic substance of natural origin having no side effect.

According to the present invention, there is provided an antihistaminic substance comprising an extract from a plant tissue of Stevia. The substance having an antihistaminic action in vivo is a component contained in the plant tissue of Stevia, mainly in its stems and leaves, and contained in a cold water, hot water or lower alcohol extract thereof. Standing of the extract naturally causes fermentation to separate one or organic acids, such as lactic acid and acetic acid, thereby more enhancing the antihistiminic action. The addition of at least one organic acid to the extract immediately after extraction can also enhance the antihistiminic action.

By using an extract an from the plant tissue of Stevia of the present invention, the harmful effects to organisms caused by excessive release of histamine can be repressed.

DETAILED DESCRIPTION OF THE INVENTION

Figure 1:
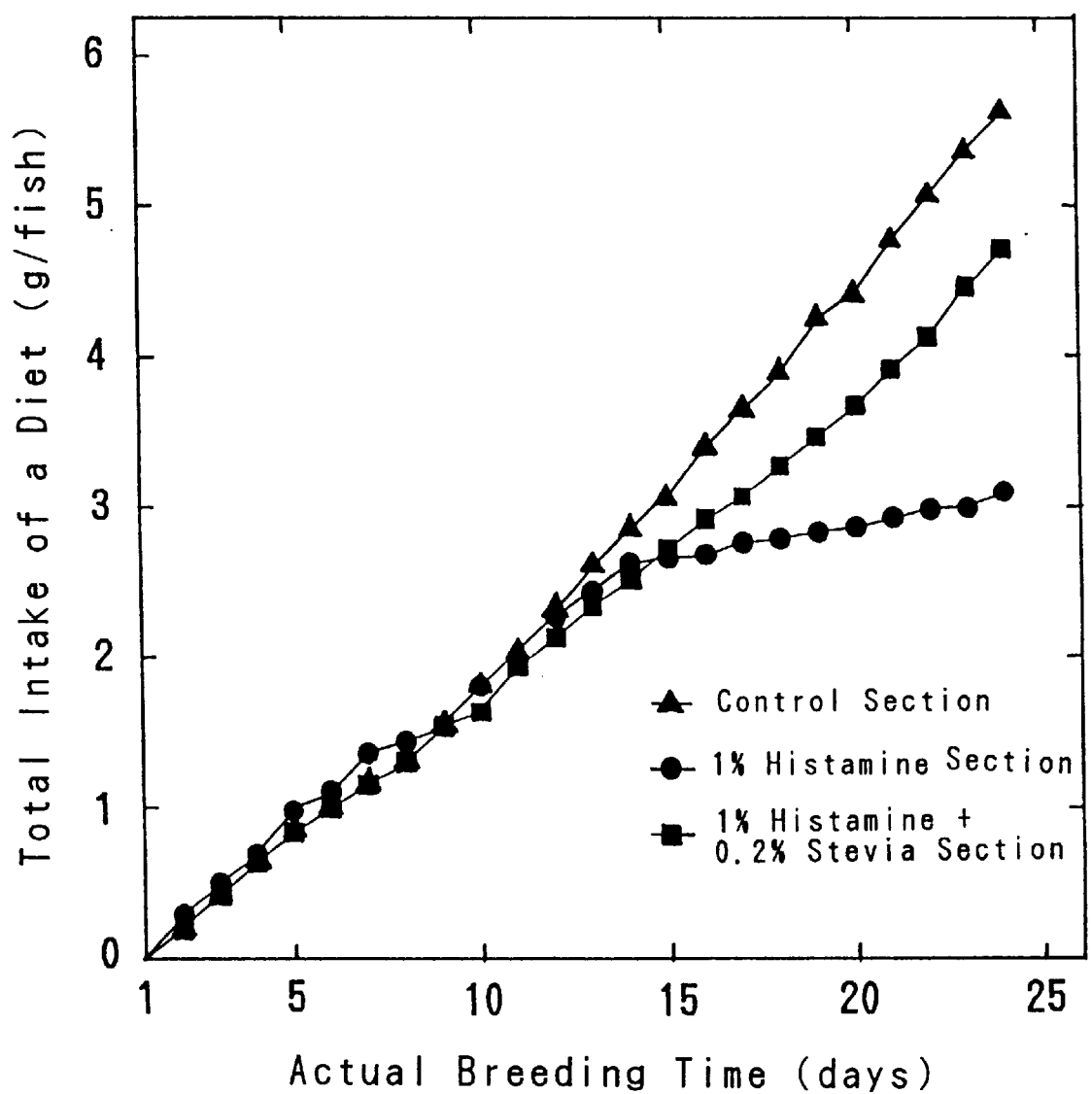
FIG. 1 is a graph showing the relationship between the total intake of rainbow trouts of a diet (g/fish) and the actual breeding time (days) thereof for each test section.

Histaminic substances as used in the present invention are chemical mediators such as histamine and leucotriene released from special cells such as mast cells as a result of the antigen-antibody reaction, and derivatives of histamine. The derivatives of histamine include, for example, dizzerosine produced by elimination of $NH_3$ from histamine and L-lysine. Excessive release of these substances from the cells and activation thereof causes vasodilatation, which is said to be responsible for flare, itch and pain.

The antihistaminic substances are substances which are physiologically antagonistic against the action of histamine and have the action of curing and relieving symptoms due to the histaminic substances.

Stevia used as a raw material in the present invention means Stevia rebaudiana Bertoni, a perennial composite originally coming from South America, and relative plants thereof. Experiments have revealed that the active principle thereof is mostly contained in the leaves and stems, particularly in the stems before formation of buds and in the stems of matured plants, but also in roots, flowers and juvenile plants. Further, the antihistaminic effect has not been observed in steviocide and revaudiocide known as the sweetening components of Stevia. Accordingly, the substance of the present invention may contain another substance as long as it contains the extract of the plant tissue of Stevia.

When the substances of the present invention are actually applied to humans and animals, all of the tissues of the plant; preferably the leaves of Stevia or the stems before formation of buds, are harvested, and pulverized after drying or without drying, followed by extraction. They may be pulverized and extracted simultaneously with harvest. In order to improve the extraction efficiency, it is preferred that they are cut and thereafter further pulverized. In general, the roots are not used for germination in the coming spring.

The active principle is contained in high concentration in a supernatant obtained after the plant tissue has been immersed in water at an ordinary temperature for 2 to 3 days. It is also contained in high concentration in a supernatant obtained by immersing the plant tissue in warm water at 30° C. to 50° C. for 3 hours, in an extract obtained by boiling it in hot water, and in an extract extracted with a lower alcohol such as methyl alcohol, ethyl alcohol, n-propyl alcohol or i-propyl alcohol.

Further, a boiled extract of the matured plant tissue of Stevia is also used.

The extract of Stevia is concentrated to use it as an extracted stock solution having a solid content of 16 to 20 W/V %. In general, 0.3 liter to 3 liters of the extracted stock solution is obtained from 1 kg of the mixture of dried stems and leaves of Stevia.

The extracted stock solution of the plant tissue of Stevia is neutral. When the extracted stock solution is stored in a container at ordinary temperature, spores of yeast existing in the plant tissue of Stevia germinate and ferment to fill the container with carbon dioxide. Accordingly, the extracted stock solution is preferably stored in a container equipped with a device for automatically releasing carbon dioxide when the internal pressure reaches a specified value.

Organic acids such as acetic acid and lactic acid are produced by fermentation, and a synergistic effect thereof with the extract component of Stevia gives the effective antihistaminic action. The antihistaminic action can be enhanced by addition of organic acid to the extract of Stebia after fermentation. Further, the antihistaminic action can also be obtained by addition of an organic acid such as acetic acid or lactic acid to the solution immediately after extraction.

The organic acids added to the extract include acetic acid, lactic acid, propionic acid, valeric acid, citric acid, tartaric acid, malic acid, maleic acid, fumaric acid and acrylic acid.

EXAMPLE 1

(1) Preparation of Test Solution of Stevia

In the spring, nursery stocks of Stevia were planted, and above-ground parts were harvested before formation of buds. After harvest, the above-ground parts were divided into leaves and stems. The leaves were finely pulverized with a pulverizer to produce a Stevia leaf powder, and the stems were cut to a size of about 5 cm and then finely pulverized with a pulverizer to produce a Stevia stem powder.

The Stevia leaf and stem powders thus obtained were compounded at a ratio of 3:7, and homogeneously mixed. The resulting Stevia mixed powder was used as a raw material for Stevia extracted stock solution.

Then, 1 kg of the Stevia mixed powder was boiled in 10 liters of water for 1 hour. After cooling, the powder was squeezed with a squeezing machine, and strained lees were separated, followed by boiling down for 3 hours to obtain 1.2 liters of an unfermented Stevia extracted stock solution. The unfermented extracted stock solution was stored in a container, and allowed to stand at 20~30° C. As a result, fermentation proceeded, and intermittent discharge of carbon dioxide was required.

The fermentation proceeded with violence in the early stages, and gradually became gentle after an elapse of 3 to 4 months. Even after an elapse of 1 year, the fermentation further continued for 3 years or more.

In this example, a Stevia extracted stock solution fermented for 1 year was used. Accordingly, the Stevia solution in this example corresponds to 1.2 $g/cm^3$ of the raw material, Stevia mixed powder. Further, the Stevia solution has a solid concentration of about 20%.

(2) Breeding of Rainbow Trouts

Rainbow trouts were bred under the following conditions:
Average weight at the start of breeding: 4.84 g
Breeding water temperature: 15±1° C.
Breeding fish tank: Plastic tank having an internal volume of 36 liters
Flow rate of water: 250 ml/minute
Number of fishes bred: 20 fishes/test section
Method of giving a diet: 3 times daily until satiation
Composition of Test Diets A commercial diet for rainbow trouts was purchased, and after pulverization, an additive or additives for testing were added thereto, followed by mixing. The mixture was reformed, and then given to the rainbow trouts. A diet containing no additive was also once pulverized and reformed.

Control Section: No additive was added to the commercial diet for rainbow trouts.

1% Histamine Section: One part by weight of histamine was added to 100 parts by weight of the commercial diet for rainbow trouts.

1% Histamine +0.2% Stevia Section: One part by weight of histamine and 0.2 part by weight (in terms of solid matter) of the Stevia test solution were added to 100 parts by weight of the commercial diet for rainbow trouts.

(3) Results of Test

With respect to the total intake of the diet per rainbow trout, 13 to 15 days after the start of breeding, the diets were satisfactorily ingested in all the sections, and no significant difference was observed between the different sections. However, after an elapse of about 15 days, the diet was well taken in the control section, whereas the diet was little taken in the 1% histamine section. On the other hand, the ingestion of the diet continued in the 1% histamine+0.2% Stevia section although inferior to that in the control section.

For each test section, the relationship between the total intake of the diet and the actual breeding time (days) is shown in FIG. 1.

Figure 2:
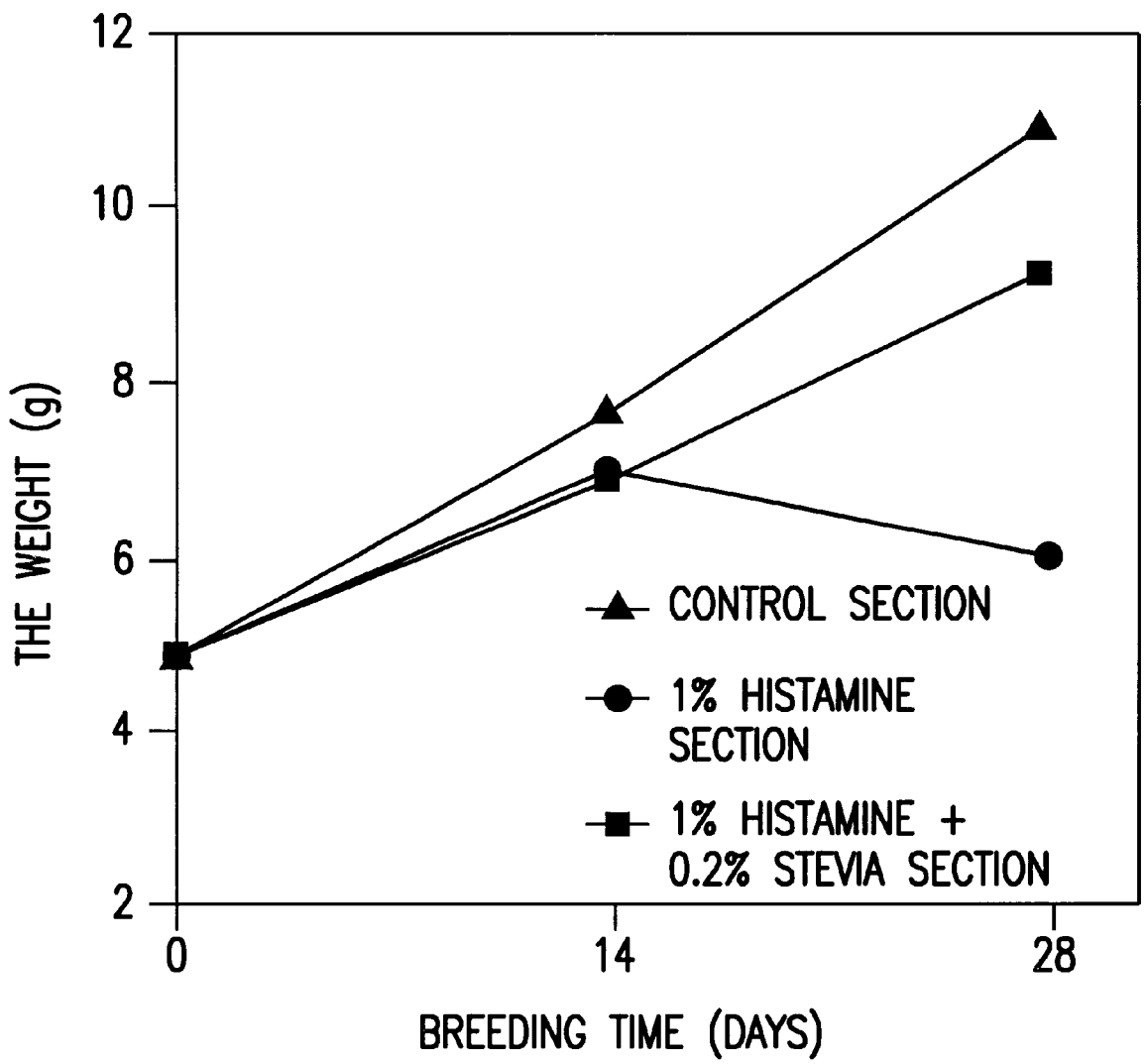
FIG. 2 is a graph showing the relationship between the breeding time (days) of rainbow trouts and the weight thereof for each test section.

At the same time, changes in weight with the breeding time (days) of the rainbow trouts were measured. Results thereof are shown in Table 1, and for each test section, the relationship between the breeding time and the weight is shown in FIG. 2. Further, the weight the rainbow trouts and the standard deviation thereof in each test section after breeding for 28 days are shown in FIG. 3.

TABLE 1

| Breeding Days (days) | Control Section | | 1% Histamine Section | | 1% Histamine + 0.2% Stevia Section | |
|---|---|---|---|---|---|---|
| | Average Weight (g) | Standard Deviation | Average Weight (g) | Standard Deviation | Average Weight (g) | Standard Deviation |
| 0 | 4.82 | 0.19 | 4.86 | 0.21 | 4.83 | 0.20 |
| 14 | 7.68 | | 6.98 | | 6.88 | |
| 28 | 10.93 | 1.2 | 6.09 | 0.57 | 9.28 | 2.24 |

Figure 3:
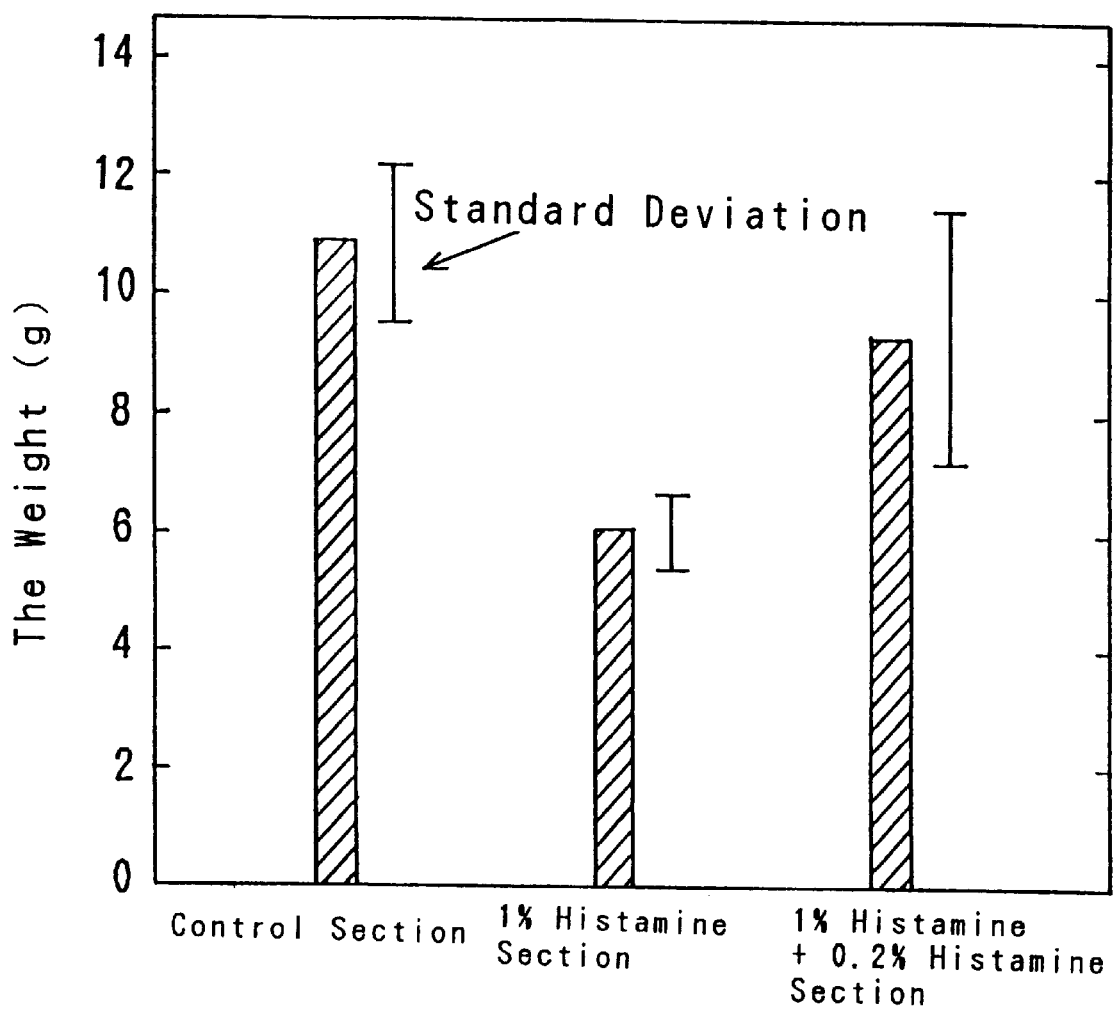
FIG. 3 is a graph showing the weight of rainbow trouts and the standard deviation thereof after breeding for 28 days for each test section.

Table 1 and FIGS. 1 to 3 show that a substance antagonistic against the action of histamine exists in the test solution of Stevia. At the same time, from the fact that the standard deviation in the 1% histamine+0.2% Stevia section is large, it is understood that the difference in the antihistaminic effect of Stevia between individuals is significant.

These rainbow trouts were dissected, the stomach was fixed in bouin solution, embedded in paraffin, sectioned and stained with hematoxylin and eosin for light microscopic observation.

In the control section, muscular layers and mucosal cells of the stomach walls in the pyloric regions were well developed, and lamina propria mucosae for supplying nutrients to the mucosal cells well extended from the muscular layers to the vicinities of leading edges of the mucosal cells. On the other hand, in the 1% histamine section, the leading edges of almost all mucosal cells were deficient. Although not deficient, the lamina propria mucosae atrophied, and the damage of tissues were observed at the leading edges of the mucosal cells. Thereafter, the decay of the tissues conceivably takes place, and it is clear that histamine is responsible for the atrophy of the lamina propria mucosae and the decay of the mucosal cells.

In the 1% histamine+0.2% Stevia section, the leading edges of the mucosal cells were scarcely deficient, and the lamina propria mucosae well extended to the leading edges of the mucosal cells.

In the 1% histamine section, crevices were observed in the mucosal cell layers in the cardiac regions, and the atrophy of the mucosal cells were observed. In the control section and the 1% histamine+0.2% Stevia section, the states of the mucosal cells were normal. In general, the deficiency of the stomach walls caused by histamine was noticeable in the pyloric regions and was slight in the cardiac regions.

The above-mentioned results revealed that the Stevia test solution had the action of repairing the atrophy, damage and decay of the tissues caused by histamine.

EXAMPLE 2

(1) Breeding of Broilers (Chickens)

Using the Stevia test solution prepared in Example 1, the detoxification of histamine in male broilers one day old was tested under the following conditions:

Average weight at the start of breeding: 40 g

Number of broilers bred: 10 broilers (8 broilers in a control section)/test section Breeding Period: 14 days Breeding conditions: in a brooder equipped with a heater, until the 7th day, and in a breeding chamber at 20 to 23° C., after the 7th day Control Section: A commercial chick starter (base diet) was purchased, and administered to the broiler.

Histamine Section: Histamine was added to the base diet so as to give a histamine concentration of 0.4%, and the resulting diet was given to the broilers.

Stevia Section: 0.4% of histamine and 0.2% of the Stevia extracted solution (in terms of solid matter of the Stevia extract) were added to the base diet, and administered to the broilers.

(2) Results of Test

The average weight of the broilers after 14 days in each section is shown in Table 2.

The weight rate of increase is clearly lowered in the histamine section, and the toxicity of histamine is significantly improved in the Stevia section. That is to say, it became clear that the addition of histamine to the diet repressed an increase in weight, but the addition of the Stevia extract counteracted the harmful effect of histamine.

TABLE 2

| Breed-ing Days (days) | Control Section | | 0.4% Histamine Section | | 0.4% Histamine + 0.2% Stevia Section | |
| --- | --- | --- | --- | --- | --- | --- |
| | Average Weight (g) | Standard Deviation | Average Weight (g) | Standard Deviation | Average Weight (g) | Standard Deviation |
| 14 | 229.8 | 26.2 | 146.6 | 34.6 | 177.0 | 26.9 |

After breeding for 14 days, the gizzard ulcer indexes were judged for the respective broilers and are shown in Table 3. The gizzard ulcer index was judged as follows:

TABLE 3

| Test Section | Judgement (broilers) | | | | Ulcer Index | |
| --- | --- | --- | --- | --- | --- | --- |
| | Index 0 | Index 1 | Index 2 | Index 3 | Average | Standard Deviation |
| Control Section | 3 | 5 | 0 | 0 | 0.63 | 0.52 |
| Histamine Section | 1 | 4 | 2 | 3 | 1.70 | 1.06 |
| Stevia Section | 4 | 3 | 2 | 1 | 1.00 | 1.05 |

Index 0: No abnormality is observed at all in a keratinoid layer, and the degree of roughening and erosion is very slight.

Index 1: Slight changes such as roughening and a disorder in the alignment of folds are observed.

Index 2: Deficiency is more clearly observed in a keratinoid layer.

Index 3: Ulceration of the gizzard is so significant that a perforation reaches the abdominal cavity.

In the histamine section, the development of erosions and ulcers in the gizzards was remarkable as shown in Table 3, wherein 3 broilers showed ulcer index 3 indicating the most serious symptom, 2 broilers showed ulcer index 2, 4 broilers showed ulcer index 1, and only one broiler showed ulcer index 0, which was judged normal.

On the other hand, in the Stevia section, one broiler showed ulcer index 3, 2 broilers showed ulcer index 2, 3 broilers showed ulcer index 1, and 4 broilers showed ulcer index 0. It became clear that the broilers of this section were considerably decreased in the development of erosions and ulcers, compared with those of the histamine section.

In the control section, the ratio of broilers showing ulcer index 0 judged normal to the total number of individuals was $3/8(37.5\%)$, whereas in the Stevia section, it was $4/10(40\%)$. Thus, the Stevia section was better than the control section. This revealed that the Stevia extract contains a component or components for maintaining the of the stomachs of humans and animals in a good state.

In addition, it is reported that the addition of 1% of the Stevia extract used in Example 1 to diets for fish raising and stock farming improved the rate of weight increase of fishes and farm animals.

Further, as an instance, gastric ulcer was cured or relieved by the administration of the Stevia extract of Example 1 twice a day in 10 ml doses.

Furthermore, by way of example, allergic diseases were cured or relieved by directly applying the Stevia extract of Example 1 into the nasal cavities or onto the flare sites of the skins feeling indisposed, or by directly instilling a diluted stock solution thereof into the itching eyes.

What is claimed is:

1. An antihistiminic substance comprising a fermented extract from a plant tissue of Stevia and an organic acid.

2. The antihistiminic substance according to claim 1, wherein said organic acid is at least one organic acid selected from the group consisting of acetic acid, lactic acid, propionic acid, valeric acid, citric acid, tartaric acid and malic acid.

3. The antihistiminic substance according to claim 1, wherein said extract is a hot water, cold water or lower alcohol extract.

4. The antihistiminic substance according to claim 1, wherein said plant tissue of Stevia is any one of a stem, leaf and mixture of a stem and a leaf of Stevia.

5. An antihistaminic substance comprising a fermented cold water extract from a plant tissue of Stevia and an organic acid.

6. The antihistiminic substance according to claim 5, wherein said organic acid is at least one organic acid selected from the group consisting of acetic acid, lactic acid, propionic acid, valeric acid, citric acid, tartaric acid and malic acid.

7. The antihistiminic substance according to claim 5, wherein said plant tissue of Stevia is any one of a stem, leaf and a mixture of a stem and a leaf of Stevia.

* * * * *